(12) United States Patent
Bouche

(10) Patent No.: US 6,176,089 B1
(45) Date of Patent: Jan. 23, 2001

(54) METHODS AND COMPOSITIONS FOR CRYOPRESERVATION OF CELLS AND TISSUES

(75) Inventor: Nicola Bouche, Lausanne (CH)

(73) Assignee: Modex Thérapeutics, Lausanne (CH)

( * ) Notice: Under 35 U.S.C. 154(b), the term of this patent shall be extended for 0 days.

(21) Appl. No.: 09/272,637

(22) Filed: Mar. 18, 1999

Related U.S. Application Data

(60) Provisional application No. 60/105,771, filed on Oct. 27, 1998, and provisional application No. 60/124,705, filed on Mar. 15, 1999.

(51) Int. Cl.[7] .............................. F25D 17/02; A01N 1/03
(52) U.S. Cl. .................... 62/64; 62/373; 435/1.3
(58) Field of Search .................. 62/64, 45.1, 51.1, 62/62, 373; 435/1.3

(56) References Cited

U.S. PATENT DOCUMENTS

| | | | |
|---|---|---|---|
| 4,473,552 | * | 9/1984 | Jost ........................................ 424/101 |
| 5,071,741 | * | 12/1991 | Brockbank ................................ 435/1 |
| 5,629,145 | * | 5/1997 | Meryman ................................ 435/1.3 |
| 5,795,711 | * | 8/1998 | Mullon et al. ............................ 435/1.1 |
| 5,863,715 | * | 1/1999 | Rajotte et al. ........................... 435/1.3 |
| 5,965,438 | * | 10/1999 | Kadkade et al. ......................... 435/420 |

FOREIGN PATENT DOCUMENTS

| | | |
|---|---|---|
| WO 93/14191 | * 7/1993 | (WO) . |
| WO 98/14058 | 4/1998 | (WO) . |

OTHER PUBLICATIONS

Karlsson et al., 65 Biophysical J 2524–2536 (1993).

* cited by examiner

*Primary Examiner*—William Doerrler
(74) *Attorney, Agent, or Firm*—Mintz Levin; Ivor R. Elrifi; John Prince

(57) ABSTRACT

The present invention provides methods and compositions for cryopreservation of cells or tissues encapsulated in a bioartificial organs, wherein the integrity and the viability of the encased cells are maintained, along with the integrity of the artificial capsule used to encase the cells. The method provides novel conditions for cryopreserving a bioartificial organ in a freezing container using a minimum volume of added cryopreservative solution necessary to maintain both the structural integrity of the jacket encasing the bioartificial organ, and the viability of the cells encased therein.

11 Claims, 7 Drawing Sheets

METHODS AND COMPOSITIONS FOR CRYOPRESERVATION OF CELLS AND TISSUES

This application claims the benefit of U.S. Provisional Nos. 60/105,771 filed Oct. 27, 1998 and 60/124,705 filed Mar. 15, 1999.

FIELD OF THE INVENTION

The present invention relates to methods and compositions for cryopreserving cells contained in a bioartificial organ. More specifically, the present invention relates to placing a bioartificial organ in a freezing container using conditions necessary to maintain both the structural integrity of the jacket encasing the bioartificial organ, and the viability of the cells encased therein.

BACKGROUND OF THE INVENTION

Cell and tissue transplantation is fast becoming an important treatment for several diseases and conditions including, but not limited to, diabetes (e.g., Janjic et al., *Pancreas* 13: 166–172, 1996), infertility (e.g., Warnes et al., *Hum Reprod* 12: 1525–1530, 1997), heart valve replacement (e.g., Feng et al., *Eur J Cardiothorac Surg* 6: 251–255, 1992), cataracts (e.g., Taylor *Cryobiology* 23: 323–353, 1986), skin replacement (e.g., De Luca et al., *Burns* 15: 303–309, 1989), and plastic and reconstruction surgery (e.g., Hibino et al., *J Craniomaxillofac Surg* 24: 346–351, 1996). Much of the advance in tissue transplantation is due to the discovery of bioartificial organs ("BAOs"). Generally, BAOs are comprised of cells which produce a desired biologically active molecule. The cells are encapsulated in a biocompatible permselective membrane or jacket to form a capsule. The pore size of the membrane is selected to permit diffusion of the biologically active molecule out of the capsule and to protect the encapsulated cells from the host's immunological system. These BAOs are well known in the art.

As cell transplantation in general, and BAOs in particular, gain wider acceptance and use, the need for long term storage of transplantable cells and tissues increases. Currently, several methods exist for the storage of cells and tissue. These methods include: (i) maintenance in tissue culture prior to transplantation, (ii) storage at refrigeration temperatures, and (iii) freeze drying. Most cells and tissues can be maintained in culture for only a few days, and are at risk for contamination by bacteria and other infectious agents. While refrigeration may prove useful for short term storage, most cells cannot be stored at refrigeration temperatures for prolonged periods or they begin to lose viability. Freeze drying is used for long term storage. However, many cells do not survive the freeze drying process.

Cryopreservation is one alternative to these methods. If not properly controlled, however, cryopreservation can lead to damage to the cells and a decrease in cell viability. Two major mechanisms of cell damage caused by cryopreservation have been reported. First, mechanical injuries to the cells are caused by formation of intracellular and extracellular ice crystal formation. See, e.g., U.S. Pat. No. 5,071,741. Damage caused by this mechanism is worse when cells are frozen at a rapid rate because rapid freezing causes an increase in the formation of intracellular and extracellular ice crystals. See, e.g., Karlsson et al., *Biophysical J* 65: 2524–2536, 1993. Penetrating cryopreservatives have been reported to alleviate damage caused by this first mechanism. See, e.g., U.S. Pat. No. 5,071,741, and Karlsson et al., *Biophysical J* 65: 2524–2536, 1993.

Second, cells may also be damaged by osmotic forces created by changing solute conditions caused by extracellular ice formation. As extracellular ice forms and continues to grow, water molecules become sequestrated within the ice, leaving solute molecules concentrated in the remaining fluidic fraction. This leads to a hyperosmotic extracellular environment. As a result of this osmotic imbalance, water transports out of the cell, causing the cells to shrink and leading to osmotic dehydration. Osmotic dehydration is exacerbated when cells are frozen at a slower rate, due to the tendency for ice crystals to form more rapidly in the extracellular medium under these conditions. Water ceases to cross the cell membrane when temperatures become sufficiently low to cause a phase transition in the cell's lipid bilayer, changing the lipid bilayer from a loosely packed alignment into a closely packed, semi-solid (gel) form with very limited permeability. See, e.g., PCT Publication No. WO 98/14058. Both penetrating and non-penetrating cryopreservatives have been reported to alleviate damage caused by this second mechanism. See, e.g., U.S. Pat. No. 5,071, 741, PCT Publication No. WO 98/14058, Karlsson et al., *Biophysical J* 65: 2524–2536, 1993.

Optimal cryopreservation techniques must strike a balance between the damage caused to cells by mechanical forces during quick freezing and the damage caused to cells by osmotic forces during slow freezing. Different optimal cooling rates have been described for different cells. It has been suggested that the different optimal cooling rates are due to the differences in cellular ice nucleation constants and in phase transition temperature of the cell membrane for different cell types. See, e.g., PCT Publication No. WO 98/14058, and Karlsson et al., *Biophysical J* 65: 2524–2536, 1993. Freezing rates between −1° C. per minute and −10° C. per minute are preferred in the art. Karlsson et al., *Biophysical J* 65: 2524–2536, 1993.

Even when using cooling rates that are sufficiently fast to avoid damage by solution effects, intracellular ice formation will begin around −50° C. Karlsson et al., *Biophysical J* 65: 2524–2536, 1993. When cells are frozen to temperatures below this level, intracellular ice nucleation is inevitable. Cells must be thawed quickly in order to avoid being extensively damaged during the thawing process by the expansive growth of these intracellular ice crystals. Warming cryopreserved cells to 37° C. in 3 to 10 seconds will quickly bypass damage due to the crystallization phase and to any subsequent osmotic shock. Karlsson et al., *Biophysical J* 65: 2524–2536, 1993.

A polymer glass transition theory has been proposed to explain how cryoprotectants work. See, e.g., PCT Publication No. WO93/14191. The transition of an aqueous solution into an amorphous solid excludes formation of ice crystals. The glass transition temperature ("Tg") of a cell's aqueous environment is the temperature wherein a given solution goes from a glassy fluid to a rubbery state. Below the Tg, in the glass phase, the extremely high viscosities in the typical amorphous glass preclude molecular diffusion and hence chemical reactions that lead to cell damage. Two potential mechanisms are proposed. In the first mechanism, cryoprotectants work extracellularly by decreasing ice crystal formation and growth, thus reducing the movement of water molecules out of the cell during the freezing process. In the second mechanism, cryoprotectants work intracellularly by permeating the cell and reducing the amount of ice formed therein, hence reducing the amount of physical injury to cell membranes and organelles at transition phase temperatures.

Glycerol and dimethyl sulfoxide ("DMSO") have become the most widely accepted cryopreservative agents. Both of these compounds have very low Tg values, −65° C. for a 40% (vol/vol) glycerol mixture and −120° C. for a 5% (vol/vol) DMSO mixture. See, e.g., PCT Publication No. WO 93/14191. However, in order to be effective for the cryopreservation of cells or tissues encapsulated in BAOs, a cryoprotectant must not only maintain the integrity of the cellular membranes and the viability of the cells, but also maintain the integrity of the artificial jackets used to encapsulate the cells. This is critical to prevent either the release of the cellular contents into a patient upon transplantation, or allow components of a patient's immune system to permeate the protective membrane barrier. Moreover, the cryoprotectant mixture must be able to cross the semipermeable membrane in order to reach the encapsulated cells.

Although DMSO is a widely used cryopreservative of cells and tissues, it is unsuitable for use with BAOs. DMSO will dissolve the artificial polymer membrane surrounding the BAO, fracturing the integrity of the artificial jackets.

Glycerol cryopreservative compositions presently used in the art are also unsuitable for use with BAOs. Glycerol must be used in high concentrations for cryopreservation, namely, 40% (vol/vol) for red blood cells in combination with other cryoprotectants (e.g., PCT Publication No. WO 93/14191), up to 60–80% (weight to volume) for cultured skin equivalents and hematopoietic stem cells (e.g., PCT Publication Nos. WO 95/07611 and WO 96/27287, respectively). While concentrated glycerol solutions may be an effective cryoprotectant for cells in suspension, the limited wetting and diffusion properties of solutions of high concentrations of glycerol (e.g., PCT Publication No. WO 96/29862) does not permit adequate cryopreservation of cells or tissues in the microenvironment of BAOs.

Thus, a need remains in the art for viable methods and compositions for the cryopreservation of cells or tissues encapsulated in BAOs. Such methods and compositions would facilitate shipping and increase the shelf-life of BAOs.

SUMMARY OF THE INVENTION

The present invention provides methods and compositions for the cryopreservation of cells or tissue in a BAOs. BAOs are incubated in the cryopreservative solution for a time sufficient for the solution to permeate the cells or tissue within the BAOs. The BAOs are then placed in a freezing container and frozen. Preferably, the shape of the freezing container is selected to minimize the interstitial volume between the BAO and the freezing container.

In a preferred embodiment, the cryopreservative solution comprises glycerol. It is contemplated that a cryopreservative solution comprises 5% to 80% glycerol. A preferred cryopreservative solution consists of 10% glycerol. In an alternative preferred embodiment, the cryopreservation solution comprises ethylene glycol. An alternative cryopreservative solution comprises 0.5 molar to 3 molar ("M") ethylene glycol. A most preferred cryopreservative solution consists of 1.5 M ethylene glycol. The remaining diluent comprises any defined media or tissue specific buffer known in the art, for example, Dulbecco's modified Eagle's medium ("DMEM") and phosphate buffered saline ("PBS"). Both glycerol and ethylene glycol are low molecular weight permeating cryoprotectants with a low Tg.

Permeation of the cryopreservative solution to the cells within the BAO may depend on the type of membrane or jacket selected for use. In an embodiment of the invention, the BAO is incubated in the cryopreservative solution for 10 minutes to 3 hours at 4° C. to 40° C. In a preferred embodiment, the BAO is incubated in the cryopreservative solution for 60 minutes at room temperature. The BAO capsule is then immediately placed in a freezing container designed to encase the BAO such that the volume of cryopreservative in the interstitial space of the jacket is minimized.

A novel step of the invention relates to the amount of cryopreservative added to occupy the interstitial space between the BAO and the freezing container. If too large a volume of cryopreservative is added, the structural integrity of the capsule would be compromised and the capsule would rupture on thawing. A preferred freezing container would comprise a flexible container able to absorb volume changes during the freeze/thaw cycles. A more preferred freezing container would be an open tube. After placing a BAO in a given freezing container, the BAO is frozen to a desired final storage temperature using a defined freezing cycle.

The freezing cycle may be dependent on the cell type contained in the BAO. The BAO may be frozen to −50° C. at a rate of −0.5° C. per minute to −2° C. per minute, followed by freezing to −90° C. at a rate of −0.5° C. per minute to −20° C. per minute. Generally, however, a preferred freezing cycle is −1° C. per minute until the BAO reaches a temperature of −50° C., followed by a freezing rate of −10° C. per minute until the BAO reaches a final storage temperature. An optional step may include a hold in the freezing cycle at the temperature predetermined as the "Tg" of solidification for the cryopreservative solution. Methods for the determination of Tg for a given solution are well known in the art. See, e.g., Karlsson et al., *Biophysical J* 65: 2524–2536, 1993. Optimal storage temperature may also be cell type-dependent. Generally, however, a final storage temperature between −50° C. and −196° C. is preferred. A final storage temperature between −80° C. to −196° C. is most preferred. Prior to use, cryopreserved BAOs are thawed in culture medium at 37° C. for 30 seconds, allowing for rapid thawing plus sufficient time to equilibrate to physiological temperature.

DETAILED DESCRIPTION OF THE INVENTION

Figure 1:
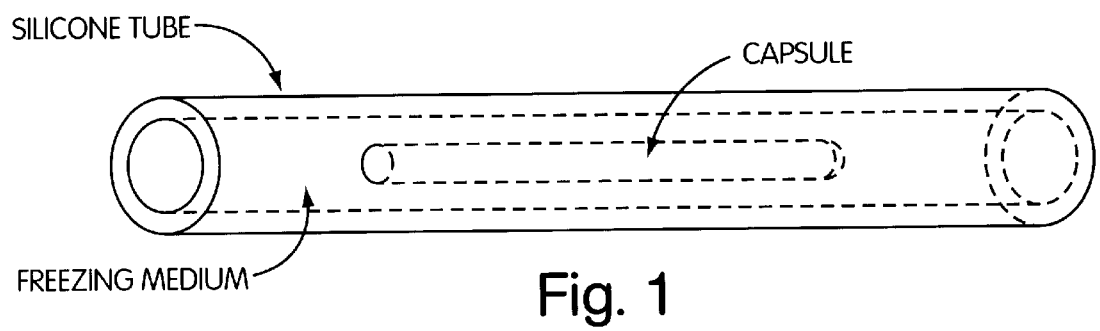
FIG. 1 is a diagrammatic representation of a freezing container. ID indicates the inner diameter of freezing container; L indicates the length of freezing container; V indicates the volume of freezing medium contained; and OD indicates the outer diameter of BAO capsule.
Figure 2A:
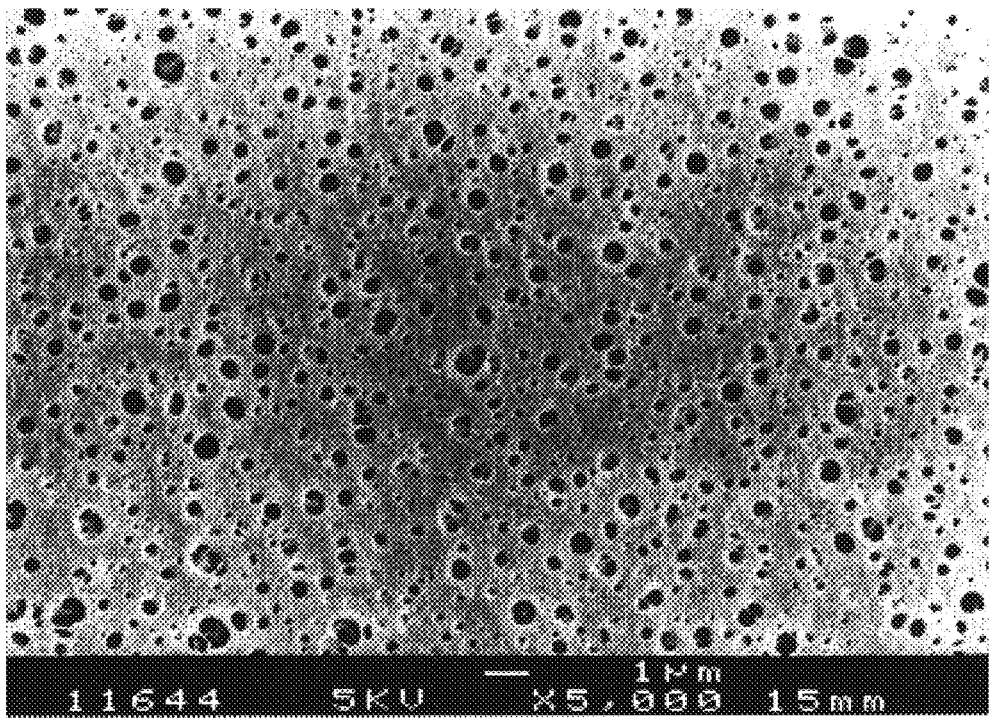
FIG. 2 is a diagrammatic representation of a scanning electron micrograph depicting frozen and nonfrozen capsule material. The panels depict the following: (A) frozen PES membrane; (B) non frozen PES membrane; (C) frozen PVA matrix; and (D) non frozen PVA matrix.
Figure 2B:
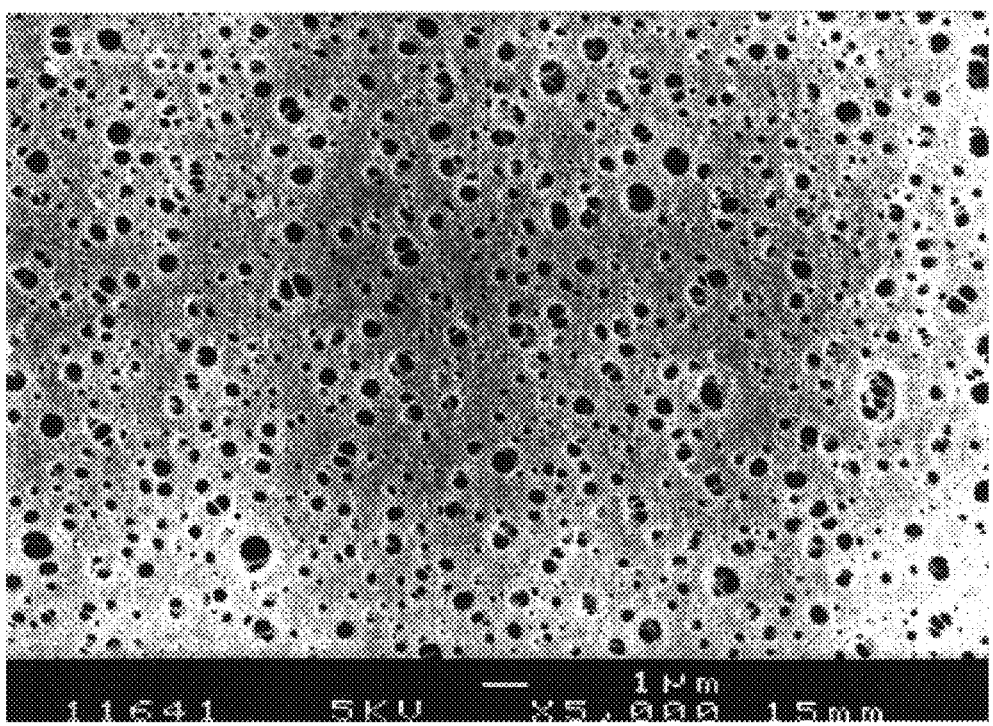
Figure 2C:
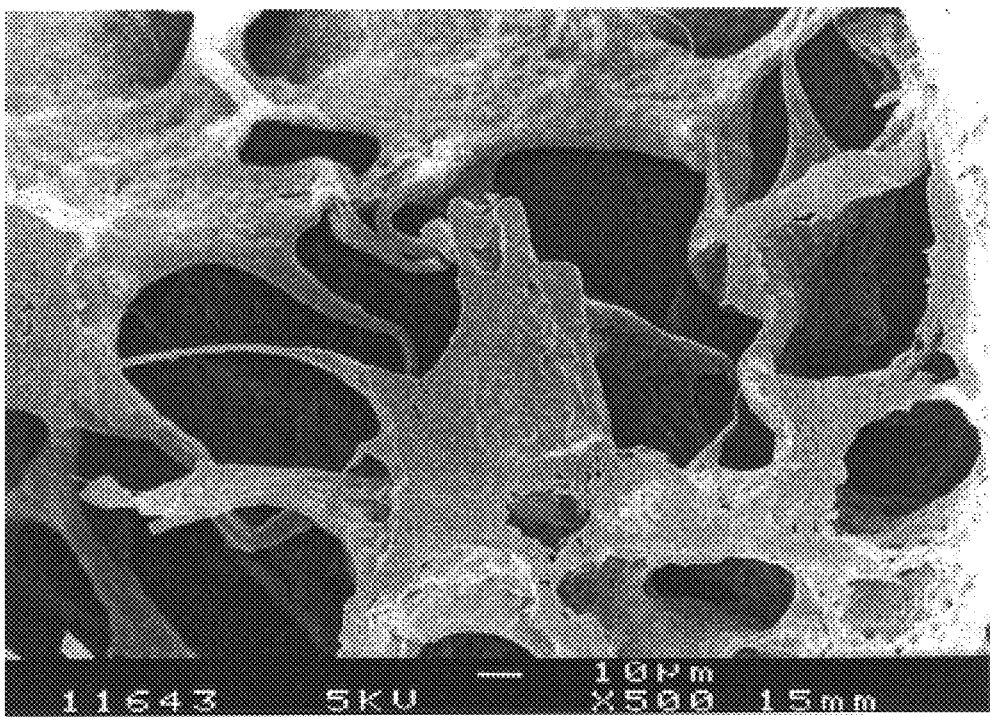
Figure 2D:
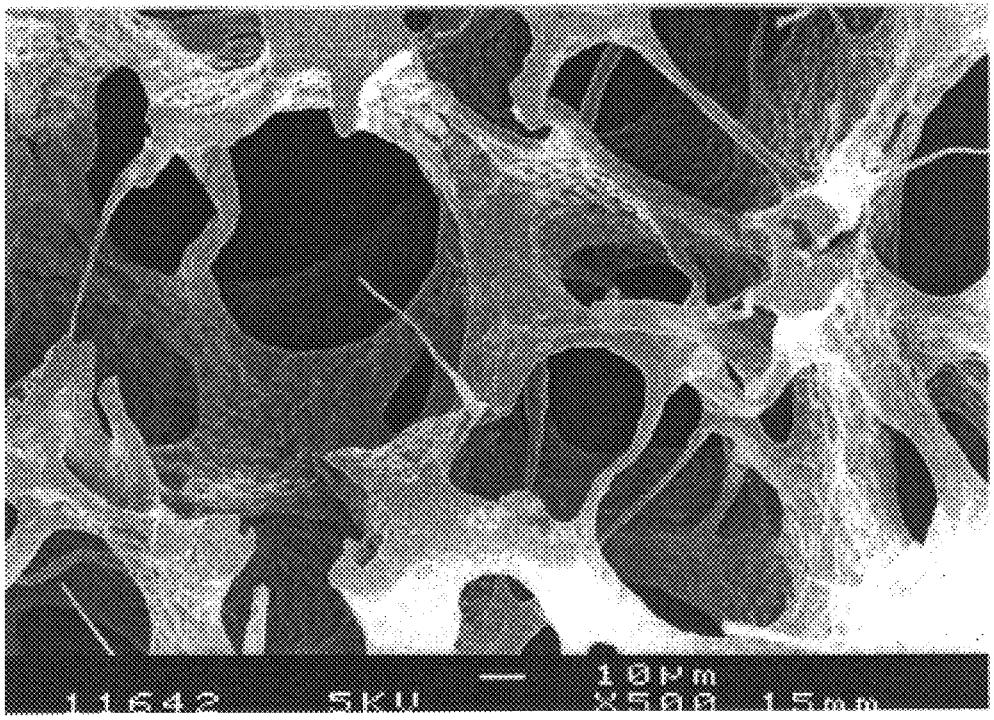

The present invention provides methods and compositions for the cryopreservation of cells or tissue in a BAOs. BAOs are incubated in a cryopreservative solution of the present invention for a time sufficient for the solution to permeate the cells or tissue within the BAOs. The BAOs are then placed in a freezing container and frozen. Preferably, the shape of the freezing container is selected to minimize the interstitial volume between the BAO and the freezing container, thereby reducing the volume of cryopreservative required. For example, as illustrated in FIG. 1, the BAO capsules used in the Examples described below had an outer diameter of 720 µm and a length of approximately 20 mm. The corresponding appropriately-sized freezing container had an inner diameter of 1.5 mm and a length of 30 mm. The interstitial volume of cryopreservative was approximately 50 µl.

In a preferred embodiment, the BAO is placed in a cryopreservative solution of 10% glycerol. In an alternative preferred embodiment, 1.5 M ethylene glycol is used as the cryopreservative solution. Both glycerol and ethylene glycol are low molecular weight permeating cryoprotectants with a low Tg. The remaining diluent comprises cell media or buffer. Several types of cell media or buffer may be used in the present invention. The type of media or buffer selected may be dependent on the cell type being cryopreserved, and these media or buffer known in the art. Suitable examples of acceptable cell media include balanced tissue culture media, DMEM, and PBS. Such media are suitable for numerous cell types. These tissue culture media may be supplemented with serum, preferably fetal calf serum (1 to 30%).

Cells or tissue may be from any source. Cells or tissue may be xenogeneic, homogeneic, syngeneic, or allogeneic. In a preferred embodiment, the cells or tissue are of human origin. Cells may express and/or secrete endogenous proteins or may be genetically engineered to express gene(s) or DNA sequence(s) from bioengineered DNA constructs.

The BAOs useful in this invention typically have at least one semipermeable outer surface membrane or jacket surrounding a cell-containing core. The jacket permits the diffusion of nutrients, biologically active molecules and other selected products through the BAO. The BAO is biocompatible, and preferably immunoisolatory. The core contains isolated cells, either suspended in a liquid medium or immobilized within a matrix. BAOs and methods of making BAOs are known in the art.

The encapsulating membrane of the BAO may be made of a material which is the same as that of the core, or it may be made of a different material. In either case, a surrounding or peripheral jacket region of the BAO which is permselective and biocompatible will be formed. The membrane may also be constructed to be immunoisolatory, if desired.

The choice of materials used to construct the BAO is determined by a number of factors and is described in detail in PCT Published Application No. WO 92/19195. Typically, the semipermeable membranes used to encapsulate cells are formed from polymeric materials such as acrylic copolymers, polyvinylidene fluoride, polyurethane isocyanates, polyalginate, cellulose acetate, ether, polyethersulfone, polyvinyl alcohols, polyacrylonitrile and mixtures or derivatives thereof. Poly(acrylonitrile-co-vinyl chloride) (PAN/PVC) is one of the common polymers used to make implantable membranes because it can easily be made into permselective membranes that allow easy transport of nutrients and greatly reduce transport of immuno-molecules. These membranes can be made with a wide variety of wall thickness and morphologies. PAN/PVC is moderately hydrophilic and is non-toxic to cells.

The jacket may have a single skin (Type 1, 2), or a double skin (Type 4). A single-skinned hollow fiber may be produced by quenching only one of the surfaces of the polymer solution as it is co-extruded. A double-skinned hollow fiber may be produced by quenching both surfaces of the polymer solution as it is co-extruded. Typically, a greater percentage of the outer surface of Type 1 hollow fibers is occupied by macropores compared to Type 4 hollow fibers. Type 2 hollow fibers are intermediate.

Numerous capsule configurations, such as cylindrical, disk-shaped or spherical are possible.

The jacket of the BAO will have a pore size that determines the nominal molecular weight cut off ("nMWCO") of the permselective membrane. Molecules larger than the nMWCO are physically impeded from traversing the membrane. Nominal molecular weight cut off is defined as 90% rejection under convective conditions. In situations where it is desirable that the BAO is immunoisolatory, the membrane pore size is chosen to permit the particular factors being produced by the cells to diffuse out of the vehicle, but to exclude the entry of host immune response factors into the BAO. Typically the nMWCO ranges between 50 and 2000 kDa, preferably between 50 and 200 kDa for BAOs encapsulating non-allogeneic cells, and preferably around 2000 kDa for BAOs encapsulating allogeneic cells. The most suitable membrane composition will also minimize reactivity between host immune effector molecules known to be present at the selected implantation site, and the BAO's outer membrane components.

BAOs may be formed by any suitable method known in the art. One such method involves coextrusion of a polymeric casting solution and a coagulant which can include biological tissue fragments, organelles, or suspensions of cells and/or other therapeutic agents, as described in PCT Published Application No. WO 92/19195 and U.S. Pat. Nos. 5,158,881, 5,283,187, 5,284,761, and 5,800,829, incorporated herein by reference.

The core of the BAO is constructed to provide a suitable local environment for the particular cells isolated therein. The core can comprise a liquid medium sufficient to maintain cell growth. Liquid cores are particularly suitable for maintaining transformed cell lines like PC12 cells. Alternatively, the core can comprise a gel matrix. The gel matrix may be composed of hydrogel, synthetic preformed matrix materials, or extracellular matrix components, including but not limited to polyethylene terephthalate (PET) or polyvinyl alcohol (PVA). See, e.g., PCT Published Application WO 92/19195, U.S. Pat. No. 5,858,810. Compositions that form hydrogels fall into three general classes. The first class carries a net negative charge (e.g., alginate). The second class carries a net positive charge (e.g., collagen and laminin). Examples of commercially available extracellular matrix components include Matrigel™ and Vitrogen™. The third class is net neutral in charge (e.g., highly crosslinked polyethylene oxide, or polyvinylalcohol).

In a preferred embodiment, the core of the BAO of the present invention is comprised of polyvinyl alcohol (PVA) or polyethylene terephthalate (PET). In another preferred embodiment, the core material of the BAO possess nonpermeating cryopreservatives properties.

Any suitable method of sealing the BAO may be used, including the employment of polymer adhesives and/or crimping, knotting and heat sealing. These sealing techniques are known in the art. In addition, any suitable "dry" sealing method can also be used. In such methods, a substantially non-porous fitting is provided through which the cell-containing solution is introduced. Subsequent to filling, the BAO is sealed. Such a method is described in U.S. Pat. Nos. 5,653,687, 5,653,688, and 5,713,887, incorporated herein by reference.

Permeation of the cryopreservative solution to the cells within the BAO may depend on the type of membrane selected for use. In a preferred embodiment, the BAO is incubated in the cryopreservative solution for 60 minutes at room temperature, placed in a freezing container designed to encase the BAO such that the volume of cryopreservative in the interstitial space is minimized, and frozen to a desired final storage temperature using a defined freezing cycle. The freezing cycle may be dependent on the cell type contained in the BAO. Generally, however, a preferred freezing cycle is −1° C. per minute until the BAO reaches a temperature of −50° C., followed by a freezing rate of −10° C. per minute until the BAO reaches a final storage temperature. Optimal storage temperature may also be cell type-dependent. Generally, however, a final storage temperature between the "Tg" and −196° C. is preferred. A final storage temperature between −90° C. to −196° C. is most preferred. Prior to use, cryopreserved BAOs are thawed in culture medium at 37° C. for 30 seconds.

In one preferred embodiment, the cryopreservative solution consists of 10% glycerol. In another preferred embodiment, the cryopreservation solution is 1.5 M ethylene glycol. In a third embodiment, the cryopreservation solution is a mixture of 10% glycerol and 1.5 M ethylene glycol. Both glycerol and ethylene glycol are low molecular weight permeating cryoprotectants with a low Tg. The remaining diluent comprises any balanced tissue culture media or suitable buffers known in the art. The selection of tissue culture medium or buffer may depend on the cell type being cryopreserved. Culture media or buffers are well known in the art. Many suitable types of mammalian tissue culture media and buffers are commercially available, for example, DMEM and PBS. Either may be used for many cell types. The diluent may be supplemented with serum, preferably fetal calf serum, between 1% to 30%. The diluent may also contain additional components chosen from the group comprising: physiologically compatible salts, carbohydrate food source, and serum albumin. See, e.g., PCT Publication No. WO 96/27287.

A novel step of the invention relates to the amount of cryopreservative added within the interstitial space between the BAO and the freezing container. If too large a volume of cryopreservative is added, the mechanical stability of the capsule would be compromised and the capsule would rupture upon thawing. In an embodiment of the invention, wherein a 20 mm long BAO is placed into a freezing container comprised of a PES#5 silicon tube of around 3 mm diameter, the volume of freezing medium required to maintain mechanical stability of the capsule would not exceed 500 $\mu$l of cryopreservative. In a preferred embodiment, the volume of freezing medium used is a volume sufficient only to "wet" or saturate the capsular volume with cryopreservant. We also contemplate an "added" volume beyond that sufficient to wet the capsule. Accordingly, such "added" volume ranges preferably between 0 $\mu$l and 200 $\mu$l. A minimum added volume of 0 $\mu$l cryopreservative is obtained by the quick transfer of the BAO capsule into a freezing container immediately after the incubation step. In another embodiment, the volume chosen is determined based on the total volume of cryopreservative in the interstitial space between the BAO membrane and a given freezing container. In yet another embodiment, the volume of cryopreservative chosen is determined based on the surface area of the BAO membrane within a given freezing container. A preferred freezing container would comprise a flexible container able to absorb volume changes of the various components during the freeze/thaw cycles. A more preferred freezing container would comprise an open tube.

After placing a BAO in a given freezing container, the BAO is frozen to a desired final storage temperature using a defined freezing cycle. Freezing rate or freezing cycle is defined as the decrease in temperature of the cell suspension per unit time. Various cell types may have different optimal freezing rates or freezing cycles. See e.g., PCT Publication No. WO 96/27287. Final storage temperature may also be dependent on cell type, but is generally known in the art to be approximately −80° C. to −196° C., the temperatures maintained by dry ice and liquid nitrogen freezers, respectively.

Once the BAOs are frozen, they may be thawed by placing them directly into culture medium at 37° C. for approximately 30 seconds. This allows for a rapid rate of thawing. In addition, said incubation time may be extended to allow the BAO to approach the physiological temperature of the culture media, if so desired.

After thawing, BAOs may be assayed for viability or may be used immediately for transplantation. Viability may be determined by histological and functional methods. Cells are assayed by histological methods known in the art, including, for example, morphological index, exclusion of vital stains, and intracellular pH.

One or more in vitro assays are preferably used to establish functionality of the BAO prior to implantation in vivo. Assays or diagnostic tests well known in the art can be used for these purposes. See, e.g., METHODS IN ENZYMOLOGY, (Abelson, Ed.), Academic Press, 1993. For example, an ELISA (enzyme-linked immunosorbent assay), chromatographic or enzymatic assay, or bioassay specific for the secreted product can be used. If desired, in vivo secretory function of an implant can be monitored over time by collecting appropriate samples (e.g., serum) from the recipient and assaying them. In one embodiment, biological activity of EPO secreted from implanted BAOs may be measured by alteration in effective hematocrit level in recipient mice. In another embodiment, an assay of EPO secretion from explanted BAOs may be performed. If the recipient is a primate, microdialysis may be used.

EXAMPLES

Example 1

Structural Integrity of Capsules

Structural integrity of capsules was assessed by scanning electron microscopy after a freeze-thaw cycle. Retention of structural integrity of capsules is important, as a breach of the structural integrity would compromise the BAO. The host's immune system could attack the core of cells within the capsule, or the cells within the membrane could escape into the host.

Capsules (20 mm in length) composed of PES#5 fibers containing PET matrix were constructed by methods known in the art. Capsules were equilibrated in a cryopreservative solution consisting of 10% glycerol in a DMEM and 10% fetal calf serum solution, and placed in freezing containers. The capsules were then frozen in a freezing cycle of –1° C. per minute until the capsules reached a temperature of –50° C., followed by a freezing rate of –10° C. until the capsules reached a final storage temperature of –90° C. The capsules were subsequently thawed at 37° C. for approximately 30 seconds.

As depicted in FIG. 2, scanning electron micrograph ("SEM") analysis revealed that PES capsules with PVA matrix retained their structural and physical integrity after the freeze-thaw cycle.

Example 2

Mechanical Stability of Capsules

Mechanical stability of capsules was assessed by hydraulic permeability after a freeze-thaw cycle. Capsules (20 mm in length) composed of PES#5 fibers contained no matrix, or were filled with PVA matrix. Equilibrated capsules were placed in freezing containers, and frozen according to the freezing cycle described in Example 1.

Figure 3:
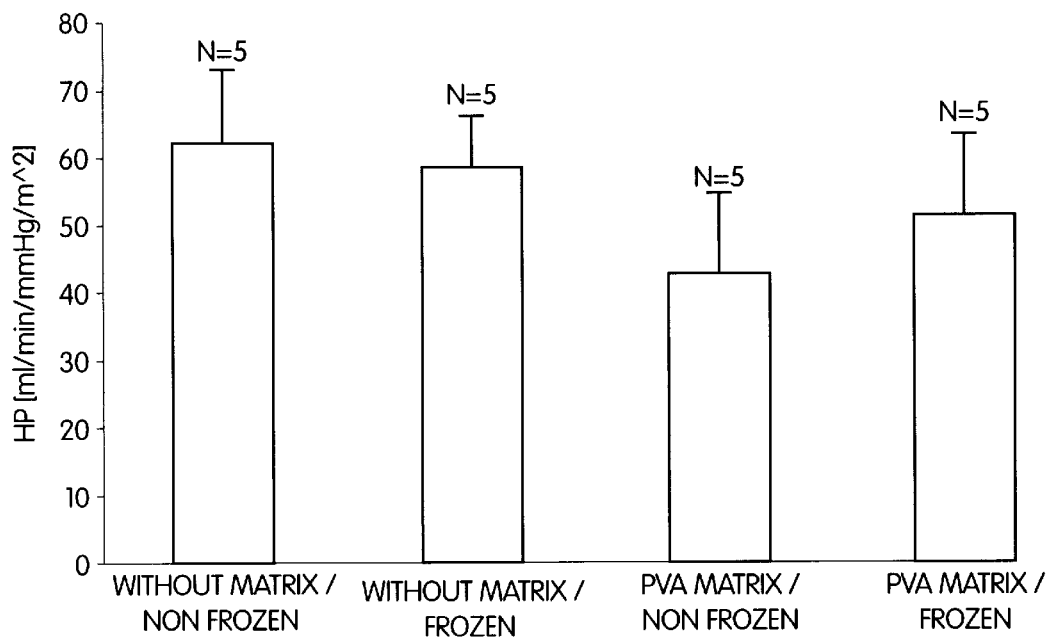
FIG. 3 is a bar graph depicting the hydraulic permeability of BAO capsules before and after a freeze-thaw cycle. Capsules were filled with no matrix or PVA matrix.

Stability was tested by hydraulic permeability of capsules to water at 0.2 bar of pressure prior to freezing and after thawing. As illustrated in FIG. 3, the hydraulic permeability of capsules that had been frozen was approximately the same as the pre-frozen capsules in both groups (i.e., no matrix or PVA matrix). Capsules filled with collagen matrix, alginate matrix, or agarose matrix and processed as described in Example 1 also maintained levels of hydraulic permeability approximately the same as pre-frozen capsules. Hence, the membrane was shown to retain its mechanical integrity during the freeze-thaw cycle.

Example 3

In Vitro Analysis of Viability of Cryopreserved BAOs

In vitro viability of cryopreserved BAOs was assessed by measuring the levels of protein secreted from frozen-thawed BAOs and compared to pre-frozen controls.

Figure 4:
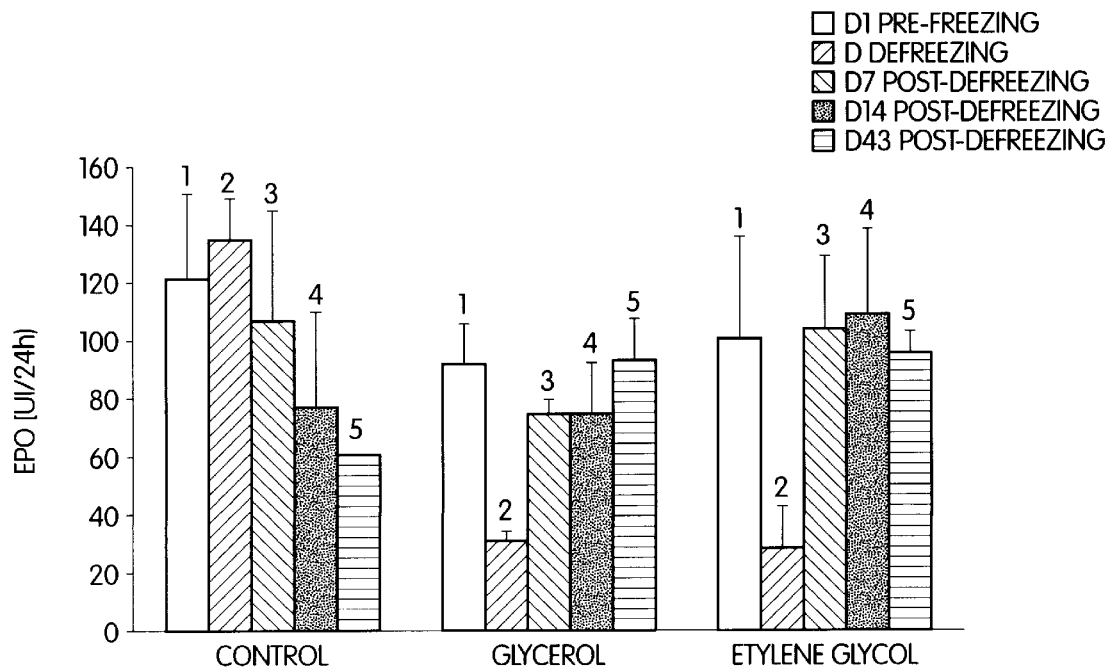
FIG. 4 is a bar graph depicting in vitro EPO release over time from BAOs containing C2C12 cells secreting mouse EPO. EPO levels were measured (1) prior to freezing; (2) immediately after defreezing; (3) seven days after defreezing; (4) 14 days after defreezing; (5) 43 days after defreezing; using non-frozen BAOs (Control), or BAOs previously cryopreserved with 10% glycerol (Glycerol), or with 1.5 M ethylene glycol (Ethylene glycol).

Recombinant C2C12 cells producing mEPO were bioengineered by methods known in the art. The mEPO-producing cells were encapsulated in a 20 mm long PES#5 capsules. As depicted in FIG. 4, EPO levels were measured (1) prior to freezing; (2) immediately after defreezing; (3) seven days after defreezing; (4) 14 days after defreezing; and (5) 43 days after defreezing. BAOs were frozen in 10% glycerol (Glycerol), or 1.5M ethylene glycol (Ethylene glycol). Nonfrozen BAOs served as controls (Control). BAOs were allowed to equilibrate in the cryopreservative solution for 60 minutes at room temperature and were then frozen in a freezing cycle of –1° C. per minute until the BAOs reached a temperature of –50° C., followed by a freezing rate of –10° C. until the BAOs reached a final storage temperature of –196° C. BAOs were stored at –196° C. for 7 days. BAOs were thawed in culture medium at 37° C. for approximately 30 seconds, were maintained in vitro in tissue culture, and were assayed for viability at prescribed times.

Samples from BAOs were assayed by ELISA to determine mEPO production. As depicted in FIG. 4, a progressive reduction in mEPO release was observed with BAOs that were not frozen (control) over the course of 7 to 43 days. In contrast, BAOs that were cryopreserved with 10% glycerol or with 1.5 M ethylene glycol showed substantially the same or better levels of mEPO release as BAOs that had never been frozen. These data indicate that the two cryopreservative solutions effectively preserved the viability of the encapsulated cells as they are as good or better than control non-frozen BAO's.

Example 4

In Vivo Analysis of Viability of Cryopreserved and Transplanted BAOs

Functional in vivo viability of cryopreserved BAOs was assessed by measuring the hematocrit levels in animals transplanted with a cryopreserved BAO at various time intervals.

BAOs containing C2C12 mEPO producing cells were produced as described in Example 3 and frozen with 1.5 M ethylene glycol, as described above. The BAOs were thawed in culture medium at 37° C. for approximately 30 seconds. Cryopreserved BAOs were implanted into DBA2J allogeneic mice. Nonfrozen BAOs served as controls. Time between thawing and implantation was approximately five minutes. The BAOs of two mice were explanted on day 14 and of one mouse on day 28. In addition, mice that had not been implanted with a BAO were included as a control. Hematocrit levels were assayed at days 0, 7, 14, 21, 28, 35, 42, 49, and 56 post-implant.

Figure 5:
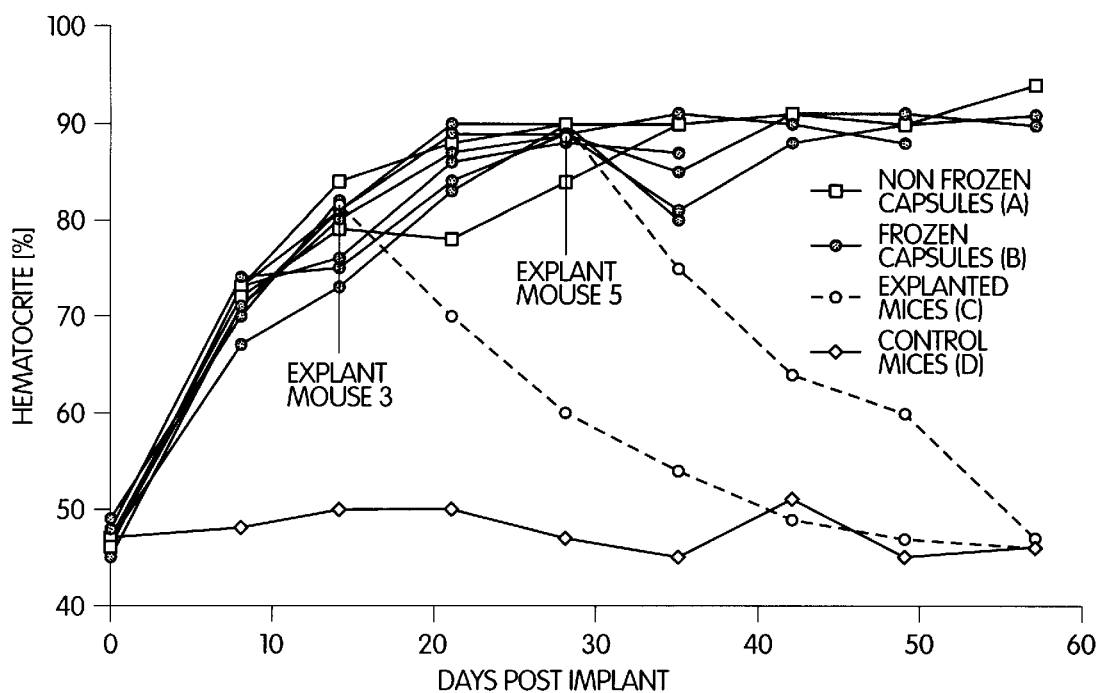
FIG. 5 is a line graph depicting the hematocrit levels over time in mice implanted with previously cryopreserved BAOs containing EPO secreting cells. Hematocrit levels were measured for 28 days in mice (A) implanted with non-frozen BAOs; (B) implanted with BAOs previously cryopreserved with 1.5 M ethylene; (C) implanted with previously cryopreserved BAOs that were explanted at day 14 or day 28; (D) with no implants.

As illustrated in FIG. 5, the cryopreserved BAOs induced a dramatic increase in the hematocrit levels of the implanted mice as compared to the control mouse. Moreover, after the BAO capsules were explanted from mice at days 14 and 28, hematocrit levels of the explanted mice decreased rapidly and began to approach the level of the non-implanted control mice. These results demonstrate that the cryopreserved cells in the BAOs remained viable and fully functional after cryopreservation.

Example 5

In Vivo Analysis of Viability of Cryopreserved and Transplanted BAOs

BAOs were prepared as described in Example 3 using recombinant mEPO expressing C2C12 cells suspended in a PVA matrix and encapsulated in a PES#5 fiber. BAOs were frozen in 1.5M ethylene glycol, as described above, or were non frozen and used as controls. Representative BAOs were either maintained in vitro in tissue culture, or were implanted in mice as described in Example 4.

BAOs maintained either in vitro in tissue culture (In vitro), or in vivo in implanted mice (In vivo). EPO levels were measured in BAOs that were (D1) nonfrozen controls; or (D15) 15 days post defreezing; (D9) 29 days post freezing; and (D157) 57 days post defreezing. Implanted BAOs were explanted from recipient mice at defined times and maintained in tissue culture for 1 day prior to being assayed for mEPO release.

Figure 6:
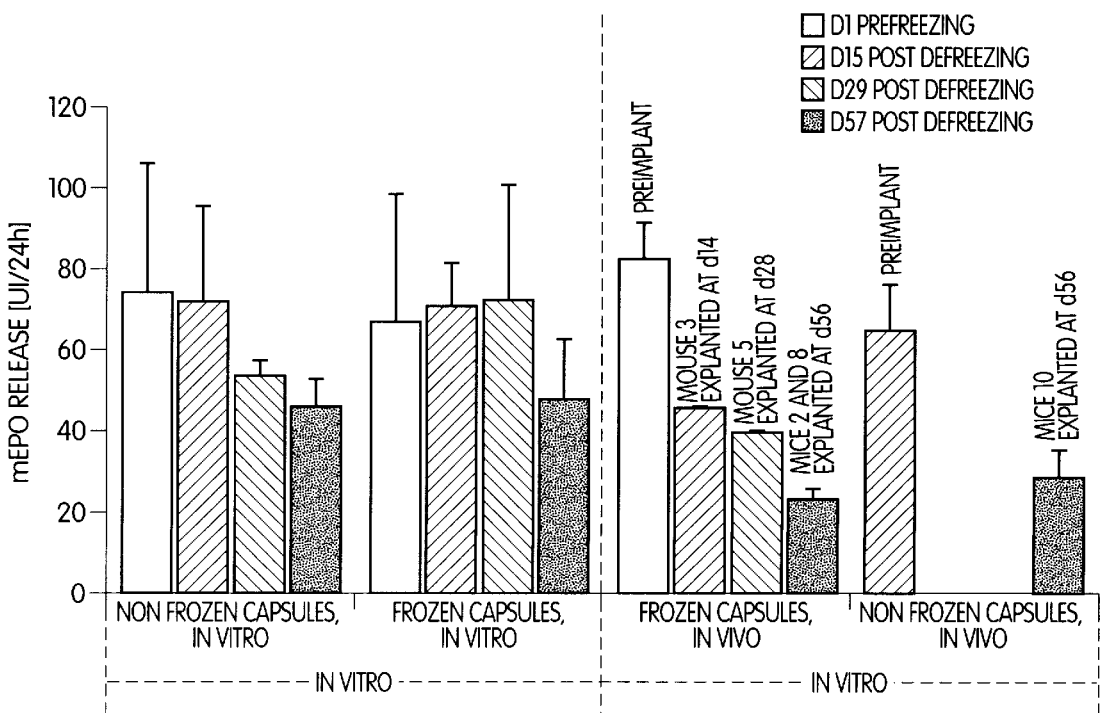
FIG. 6 is a bar graph depicting mEPO release over time from BAOs containing EPO secreting cells. EPO levels were measured in BAOs (D1) nonfrozen, pre-implant; (D15) 15 days post defreezing; (D9) 29 days post freezing; and (D57) 57 days post defreezing; in BAOs maintained either (In vitro) in vitro in tissue culture, or (in vivo) in vivo in implanted mice and then explanted and maintained in tissue culture for 1 day.
Figure 7:
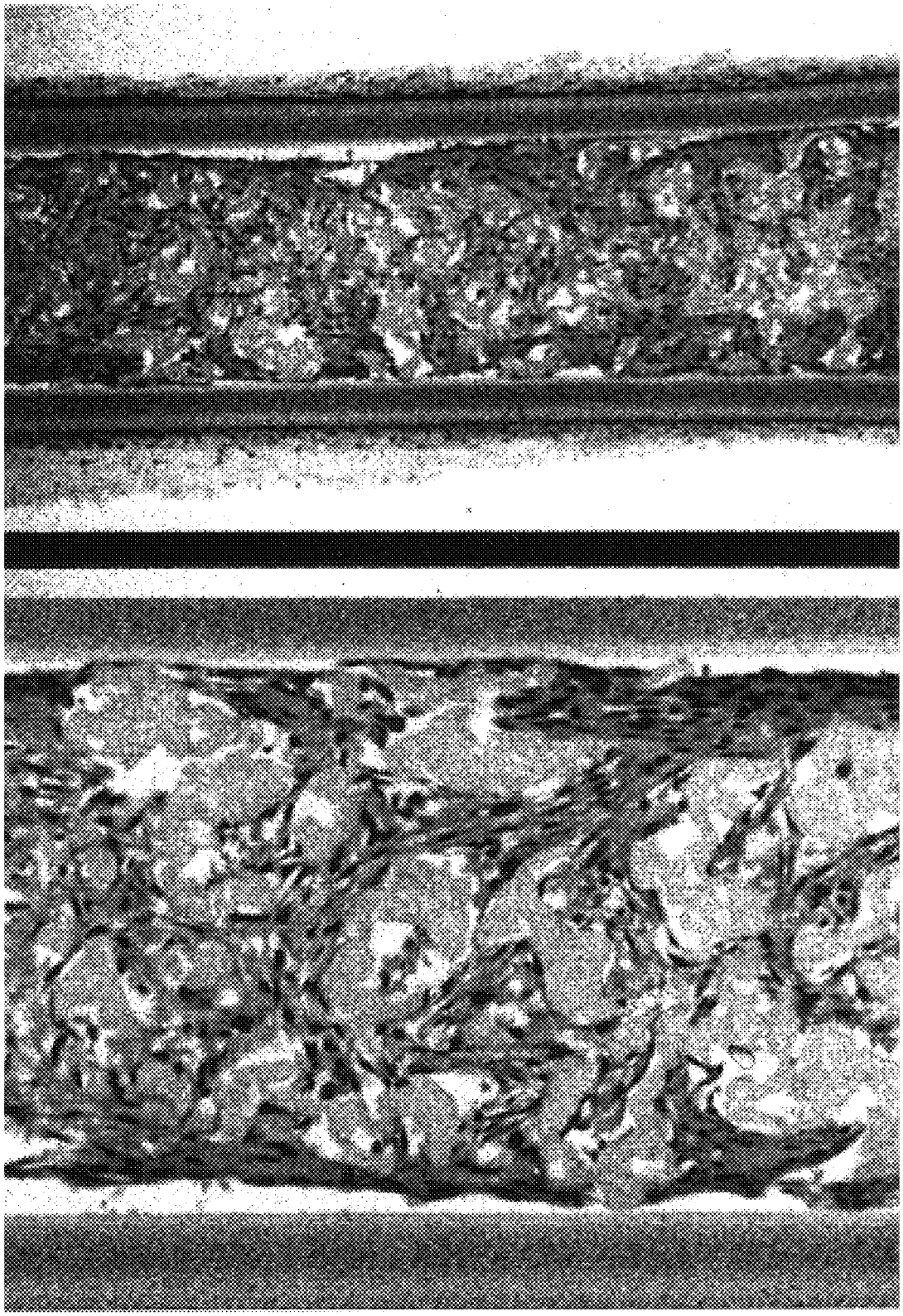
FIG. 7 is a depiction of a micrograph showing a cross-section of a BAO at low magnification (top panel) and high magnification (bottom panel). The encased cells are clearly suspended in a matrix within the BAO and surrounded by an intact membrane.

As depicted in FIG. 6, a progressive reduction in mEPO release was observed over the course of 57 days with not frozen (control) BAOs maintained in vitro. In contrast, in vitro maintained BAOs that were cryopreserved with 1.5 M ethylene glycol showed substantially the same or better levels of mEPO release than the BAO controls. These data indicate that the cryopreservative solution effectively preserved the viability and bioactivity of the encapsulated cells at levels as good or better than control non-frozen BAO's. In vivo, the previously cryopreserved BAOs maintained significant levels of mEPO release over the course of 57 days post implant, and were comparable to implanted non frozen control BAOs. These results demonstrate that the cryopreserved cells in the BAOs remained viable and fully functional after cryopreservation.

Example 6

Volume of Cryopreservative in the Interstitial Space

Figure 8:
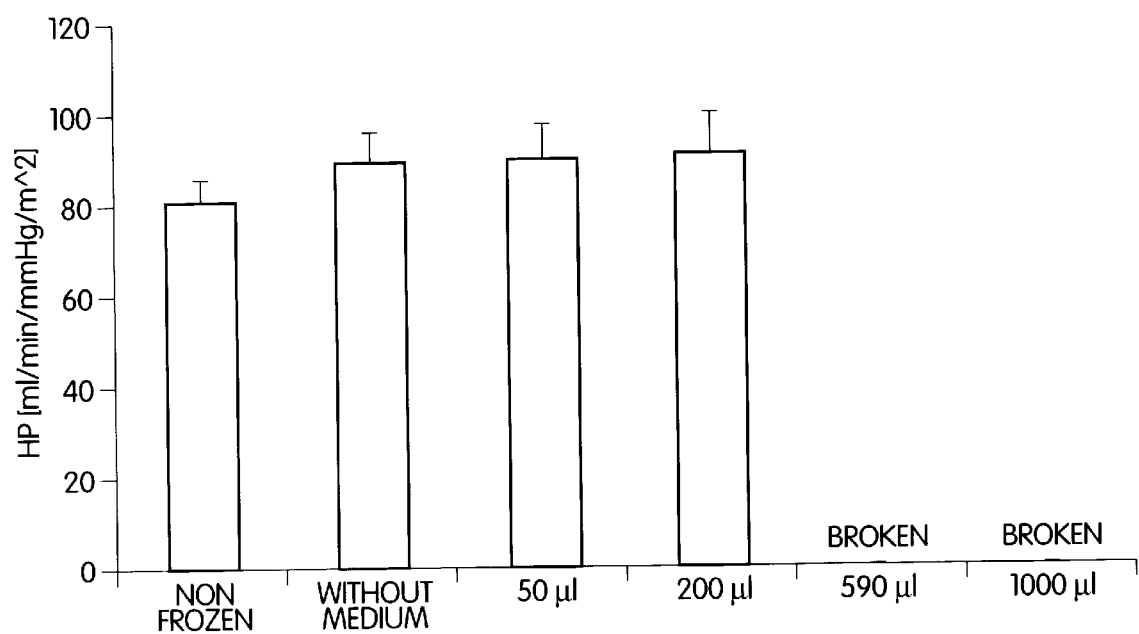
FIG. 8 is a bar graph depicting the volume requirements for added cryopreservative in the interstitial space between the BAO capsule and the freezing container. Structural integrity of BAO membranes were tested on control BAOs (non frozen) and BAOs frozen with increasing volumes of cryopreservative in the interstitial space of the freezing container. Volumes ranged from 0 µl (Without medium) to 1 ml (50 µl, 200 µl, 590 µl, and 1000 µl). Capsules that did not retain their structural integrity are noted (Broken).

BAOs were prepared and tested for hydraulic permeability as described in Example 2, with the further step of adding increasing volumes of cryopreservative solution to the interstitial space between the frozen BAO capsule and the freezing container. As shown in FIG. 8, volumes ranged from 0 µl (without medium) to 50 µl, 200 µl, 590 µl, and 1000 µl. Added volumes of cryopreservative equal to or in excess of 590 µl proved detrimental to the mechanical stability of the BAO jacket, and structural integrity of the capsule was lost (Broken).

EQUIVALENTS

From the foregoing detailed description of the specific embodiments of the invention, it should be apparent that unique methods and compositions for cryopreservation of cells or tissues encapsulated in a bioartificial organs have been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims. For instance, the choice of the particular freezing cycle, or the particular cell to be cryopreserved is believed to be a matter of routine for a person of ordinary skill in the art with knowledge of the embodiments described herein.

What is claimed is:

1. A method of cryopreservation of a bioartificial organ comprising the steps of:
   (a) incubating a bioartificial organ in a cryopreservative solution,
      (i) wherein the bioartificial organ comprises
         (A) cells macroencapsulated by
         (B) a biocompatible semipermeable membrane or jacket, wherein the cells are either suspended in a liquid medium or immobilized within a matrix, and
         wherein the pore size of the membrane or jacket permits diffusion of a biologically active molecule out of the bioartificial organ, and
      (ii) wherein the bioartificial organ is incubated for a time sufficient for the cryopreservation solution to permeate the cells of the bioartificial organ;
   (b) placing said bioartificial organ in a freezing container with a minimum volume of cryopreservative solution sufficient to wet the bioartificial organ within said freezing container; and
   (c) freezing the bioartificial organ in the freezing container of step (b), whereupon thawing of the bioartificial organ, the cells encapsulated in the bioartificial organ of step (a) are viable and the structural integrity of the semipermeable membrane of the bioartificial organ of step (a) is maintained.

2. The method of claim 1, wherein the walls of the freezing container are comprised of a flexible material able to adjust to volume changes undergone by the bioartificial organ due to volume changes in the cryopreservative solution during the freezing conditions of step (c).

3. The method of claim 2, wherein the freezing container is an open tube.

4. The method of claim 1, wherein an additional volume of cryopreservative solution beyond that necessary to wet the bioartificial organ is administered in step (b), said additional volume being between 0 µl to 200 µl.

5. The method of claim 1, wherein the cryopreservative solution is chosen from the group comprising 10% glycerol and 1.5 M ethylene glycol.

6. The method of claim 1, wherein the incubation time of step (a) is 60 minutes.

7. The method of claim 1, wherein the bioartificial organ is frozen at a freezing rate of −1° C. per minute until the cell suspension reaches a temperature of −90° C., followed by a freezing rate of −10° C. per minute until the bioartificial organ reaches a final storage temperature.

8. The method of claim 7, wherein the final storage temperature is between −90° C. and −196° C.

9. The method of claim 1, wherein the final storage temperature is between −50° C. and −90° C.

10. The method of claim 1, wherein the bioartificial organ is frozen in a freezing container shaped to provide a minimum volume of cryopreservative solution in the interstitial space between bioartificial organ and the freezing container.

11. A method of cryopreservation of a bioartificial organ comprising the steps of:
   (a) incubating a bioartificial organ in a cryopreservative solution,
      (i) wherein the bioartificial organ comprises
         (A) cells macroencapsulated by
         (B) a biocompatible semipermeable membrane or jacket, wherein the cells are either suspended in a liquid medium or immobilized within a matrix, and
         wherein the pore size of the membrane or jacket permits diffusion of a biologically active molecule out of the bioartificial organ, and
      (ii) wherein the bioartificial organ is incubated for a time sufficient for the cryopreservation solution to permeate the cells of the bioartificial organ;
   (b) placing said bioartificial organ in a freezing container containing a defined added volume of cryopreservative solution within the interstitial space of said freezing container; and
   (c) freezing the bioartificial organ in the freezing container of step (b), whereupon thawing of the bioartificial organ, the cells encapsulated in the bioartificial organ of step (a) and the structural integrity of the semipermeable membrane of the bioartificial organ of step (a) is maintained.

* * * * *